US010136837B2

(12) United States Patent
Brugnoli et al.

(10) Patent No.: US 10,136,837 B2
(45) Date of Patent: Nov. 27, 2018

(54) DEVICE AND METHOD FOR THE ANALYSIS OF THE AIR EXHALED BY A SUBJECT IN ORDER TO MEASURE THE BASAL METABOLISM THEREOF

(71) Applicant: COSMED S.R.L., Rome (IT)

(72) Inventors: Paolo Brugnoli, Pavona di Albano (IT); Alberto Di Pietro, Pavona di Albano (IT); Marco Ragusa, Pavona di Albano (IT); Domenico Celentano, Pavona di Albano (IT)

(73) Assignee: COSMED S.r.l., Roma (IT)

( * ) Notice: Subject to any disclaimer, the term of this patent is extended or adjusted under 35 U.S.C. 154(b) by 148 days.

(21) Appl. No.: 15/299,510

(22) Filed: Oct. 21, 2016

(65) Prior Publication Data

US 2017/0112413 A1     Apr. 27, 2017

(30) Foreign Application Priority Data

Oct. 23, 2015   (IT) .................. 102015000064894

(51) Int. Cl.
*A61B 5/08*     (2006.01)
*A61B 5/083*    (2006.01)
(Continued)

(52) U.S. Cl.
CPC ............ *A61B 5/0833* (2013.01); *A61B 5/083* (2013.01); *A61B 5/087* (2013.01); *A61B 5/0836* (2013.01);
(Continued)

(58) Field of Classification Search
CPC ......... A61B 5/083; A61B 5/087; A61B 5/097; A61B 5/0833; A61B 5/0836; A61B 2560/0223
See application file for complete search history.

(56) References Cited

U.S. PATENT DOCUMENTS 4,572,208 A      2/1986  Cutler et al.
6,468,222 B1 *  10/2002  Mault ................. A61B 5/0833
                                                      600/529

(Continued)

FOREIGN PATENT DOCUMENTS

EP           2 769 673         8/2014

OTHER PUBLICATIONS

IT Search Report for UB20155114 dated Jun. 13, 2016, 2 pages.

*Primary Examiner* — Navin Natnithithadha
*Assistant Examiner* — Eric J Messersmith
(74) *Attorney, Agent, or Firm* — Nixon & Vanderhye P.C.

(57) ABSTRACT

A device and a method for the analysis of the air exhaled by a subject in order to measure basal metabolism of the subject comprise a main line for a sampling flow of the air exhaled by a subject who breathes spontaneously or a subject undergoing assisted pulmonary ventilation. A mixing mini-chamber is provided for mixing a plurality of air sampling flows exhaled by the subject within a number of respiratory cycles. Sensors for sensing the oxygen concentration and the carbon dioxide concentration respectively measure the oxygen concentration and the carbon dioxide concentration within the air flow in the main line. The device further comprises an electronic control unit which processes signals from the sensors for obtaining a measurement of metabolism of the subject within a number of respiratory cycles. The electronic control unit is further programmed for automatically starting, upon switching on the device, a self-calibration stage of the device, by connecting the main line to a calibration line while causing the calibration flow to pass through a by-pass line by-passing the mixing mini-chamber, so that the calibration can be performed immediately, without requiring a filling of the mixing mini-chamber.

14 Claims, 3 Drawing Sheets

Figure 1:
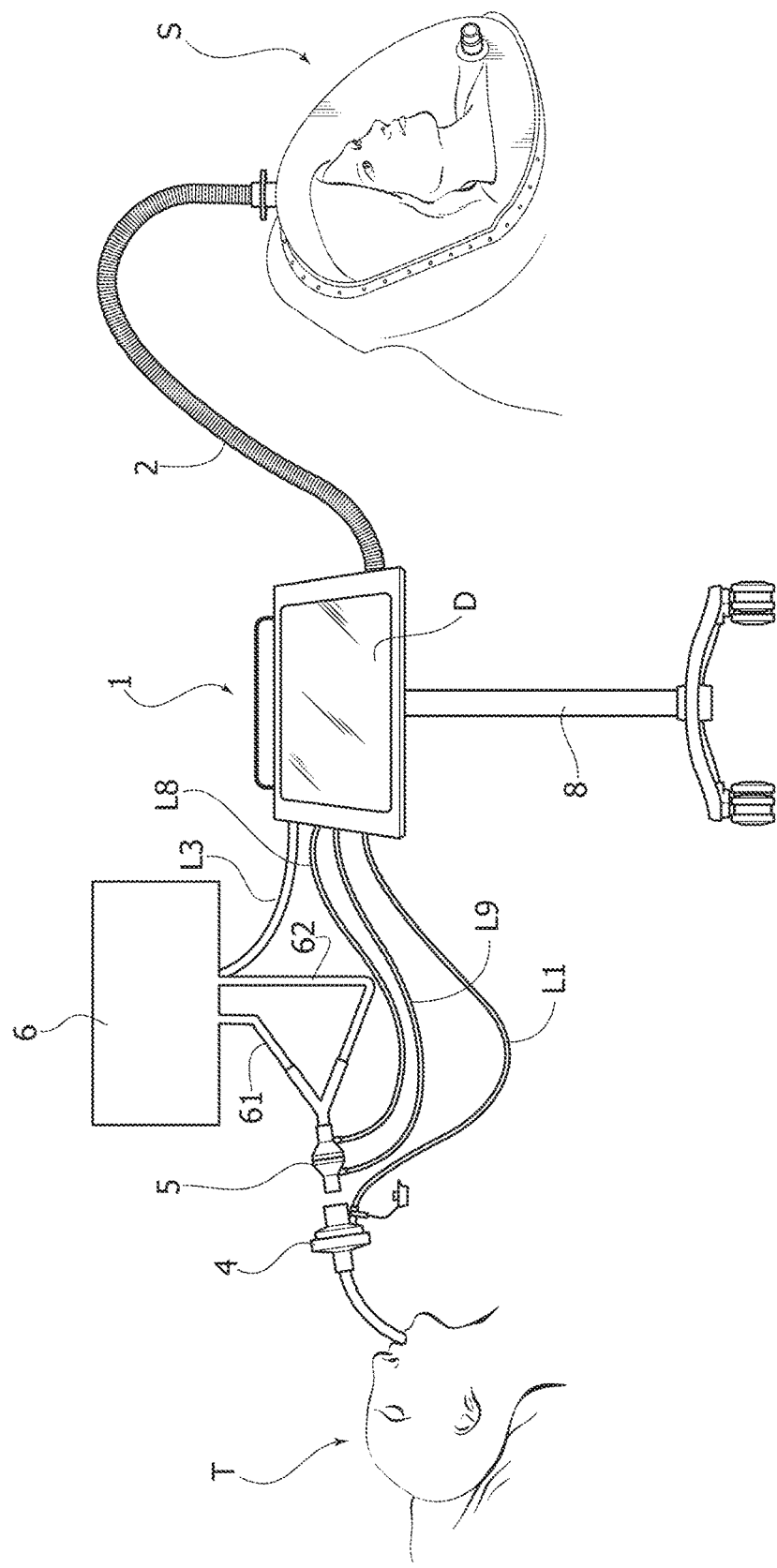

(51) Int. Cl.
*A61B 5/087* (2006.01)
*A61B 5/097* (2006.01)
*G01N 33/497* (2006.01)

(52) U.S. Cl.
CPC .......... *A61B 5/097* (2013.01); *G01N 33/497* (2013.01); *A61B 5/0803* (2013.01); *A61B 2505/03* (2013.01); *A61B 2560/029* (2013.01); *A61B 2560/0223* (2013.01); *G01N 2033/4977* (2013.01)

(56) References Cited

U.S. PATENT DOCUMENTS

2003/0216660 A1* 11/2003 Ben-Oren .............. A61B 5/083
 600/532
2014/0235961 A1* 8/2014 Brugnoli ................ A61B 5/087
 600/301

* cited by examiner

DEVICE AND METHOD FOR THE ANALYSIS OF THE AIR EXHALED BY A SUBJECT IN ORDER TO MEASURE THE BASAL METABOLISM THEREOF

This application claims priority to IT Patent Application No. 102015000064894 filed Oct. 23, 2015, the entire content of which is hereby incorporated by reference.

FIELD OF THE INVENTION

The present invention relates to devices for the analysis of the air exhaled by a subject, aimed to measure the basal metabolism of the subject. In particular the invention relates to a device of a known type including:
- a main line, for passage of a sampling flow of the air exhaled by the subject,
- a suction pump having a substantially constant flow rate, said pump being arranged downstream of the main line, for drawing said sampling air flow into the main line,
- a mixing mini-chamber interposed in the main line upstream of the suction pump for accumulating or mixing with each other a plurality of air sampling flows exhaled by the subject within a number of respiratory cycles,
- a by-pass line arranged in parallel to the mixing mini-chamber through which the air flow can flow without passing through said mixing mini-chamber,
- a by-pass valve interposed in the main line (L) downstream of the mixing mini-chamber and selectively displaceable in two different positions for causing the air flow through the main line to flow either through the mixing mini-chamber or through said by-pass line,
- first sensor means for sensing the oxygen concentration and second sensor means for sensing the carbon dioxide concentration, said first and second sensor means being arranged in the main line between said by-pass valve and the suction pump, for measuring the oxygen concentration and the carbon dioxide concentration within the air flow through the main line downstream of the mixing mini-chamber,
- a first switching valve for switching the suction inlet of the suction pump between a condition of connection to said first and second sensor means and a condition in which this connection is interrupted,
- flow measuring means for detecting the flow rate of the air inhaled or exhaled by the subject, and
- an electronic control unit configured for receiving and processing signals emitted by said first sensor means of the oxygen concentration, by said second sensor means of the carbon dioxide concentration and by said flow measuring means, so as to obtain a measurement of oxygen consumption and carbon dioxide production by the subject within a number of respiratory cycles,

PRIOR ART

A device of the above indicated type has been disclosed in document EP 2 769 673 A1 of the same Applicant. This known solution relates to devices for measuring the oxygen consumption and the production of carbon dioxide by a subject through a technique involving instantaneous "breath-by-breath" measurements or through a technique involving average measurements within a number of respiratory cycles. "Breath-by-breath" detecting devices have been produced and marketed by the Applicant since long.

The devices of this type are commonly known also as "metabolimeters" or "indirect carolimeters" and are characterized for that they enable the oxygen consumption and the production of carbon dioxide to be measured through the "indirect carolimetry" technique.

All metabolic processes which occur in the human body generate heat. As a result, the heat production and the metabolism are directly related to each other. The chemical reactions which develop energy require oxygen. Therefore from the measurement of the oxygen consumption, an estimate of the energetic metabolism of a subject can be obtained. A precise estimate of the basal metabolism can be for example required in order to properly dose enteral or parenteral nutrition of a patient.

OBJECT OF THE INVENTION

The main object which is at the base of the present invention is that of providing a single device, especially for clinical applications, which is able to provide average measurements of the oxygen consumption and the production of carbon dioxide by a subject within a number of respiratory cycles both for patients undergoing assisted pulmonary ventilation and for patients which are able of breathing spontaneously.

A further object of the present invention is that of providing a device which is simple, efficient, of reduced dimensions and easily portable by a user.

Also a further object of the invention is that of providing a device which avoids long warm-up times prior to the measuring operation which must be carried out on a subject, through the ability of performing automatic calibration rapidly.

Another object of the invention which is equally important is that of providing a device which is able of performing semi-automatic calibration operations on a disposable flowmeter by using an air flow with a known flow rate at the inlet of the device, so as to avoid the use of a calibration syringe and with no prejudice to the hygiene of the disposable flowmeter which is required for clinical applications.

SUMMARY OF THE INVENTION

In view of achieving the above indicated objects, the invention provides a device having all the features indicated at the beginning of the present description and further characterised in that said device further comprises:
- a first inlet connector connected to a system for taking a flow of air exhaled by a subject who breathes spontaneously,
- a second inlet connector connected through a sampling line to a system for taking a flow of air exhaled by a subject undergoing assisted pulmonary ventilation,
- a selection valve interposed in the main line upstream of the mixing mini-chamber for selectively connecting said first connector or said second connector to said main line,
- said selection valve having an outlet connected to the main line, a first inlet connected to said first connector and the second inlet for connection to said second connector,
- a calibration line, which receives a calibration flow, to be used for calibrating said first and second sensor means for sensing the oxygen concentration and the carbon dioxide concentration,
- a second switching valve adapted to be switched between a sampling state and a calibration state, said switching valve being controlled by said electronic control unit for selectively connecting said second inlet of said selection valve to said sampling line connected to said second connector or to said calibration line, a plurality of selector valves distributed in series along said calibration line for selectively connecting the calibration line each time to one only among a plurality of auxiliary lines adapted to provide respective calibration data, said electronic control unit being configured so that, during normal operation of the device, the selection valve is switched for feeding to the main line either a sampling flow of the air exhaled by a subject who breathes spontaneously or by a subject which undergoes assisted pulmonary ventilation, said by-pass valve being in a position causing the air flow to pass through said mixing mini-chamber so that said electronic control unit is able to perform said processing in order to obtain said measurement of the oxygen consumption and the carbon dioxide production by the subject within a number of respiratory cycles, said electronic control unit (E) being further programmed for automatically starting, upon switching on the device, a self-calibration stage of the device in which:

the second switching valve communicates said second connector of said selection valve to said calibration line while the selection valve communicates its second inlet to said main line, so that the main line enters into communication with said calibration line, said electronic control unit being configured so that in said self-calibration stage the by-pass valve is in a position which causes said sampling flow of the air exhaled by the subject to flow through said by-pass line, without passing through said mixing mini-chamber, whereby the self-calibration stage can be carried out immediately on the basis of the flow coming from said calibration line, without requiring a filling of said mixing mini-chamber.

Moreover, the present invention also provides a method for the analysis of the air exhaled by a subject, aimed to measure the basal metabolism of the subject, with the use of the above described device.

Due to these features, the device according to the invention is able of performing an average measurement of basal metabolism, both on subjects who are able of breathing spontaneously and on subjects which undergo assisted pulmonary ventilation, while avoiding long warm-up waiting times through the adoption of quick self-calibration operations.

The electronic control unit is programmed for automatically starting, upon switching-on of the device, a self-calibration stage of the device by connecting the main line to the calibration line while causing the calibration flow to pass through the by-pass line, i.e. by-passing the mixing mini-chamber (10), so that the calibration can be performed immediately, without requiring a filling of the mixing mini-chamber and thus avoiding long warm-up waiting times.

The device according to the present invention is also able of performing a semi-automatic calibration operation on a disposable flowmeter which is used along a line feeding air to a ventilated subject, so as to avoid the use of a calibration syringe and with no prejudice to the hygiene of the flowmeter, which is mandatory for clinical applications.

Further features and advantageous of the invention will become apparent from the description which follows, given purely by way of non limiting example, with reference to a preferred embodiment of the invention.

DETAILED DESCRIPTION OF A PREFERRED EMBODIMENT

Figure 2:
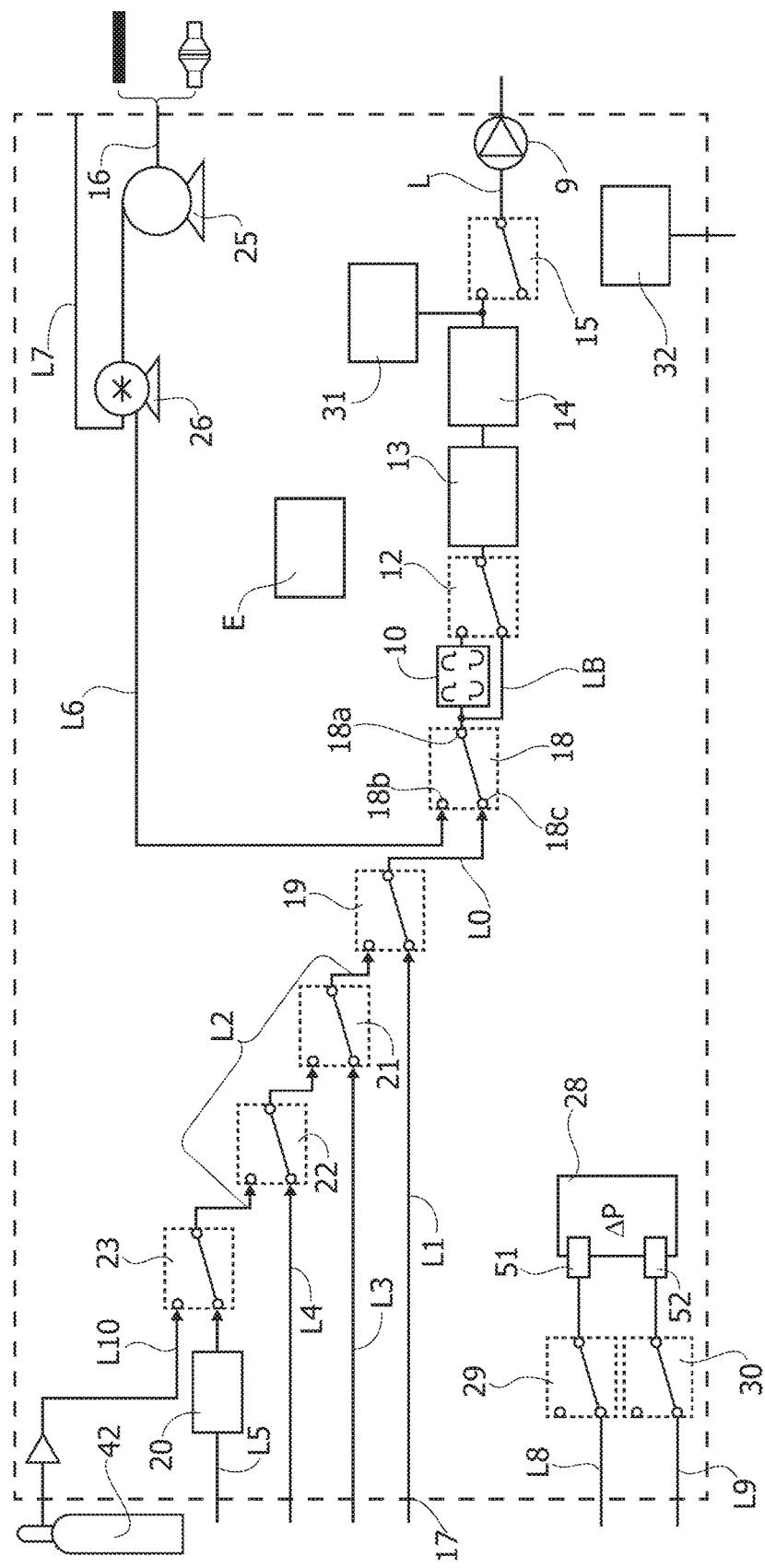
Figure 3:
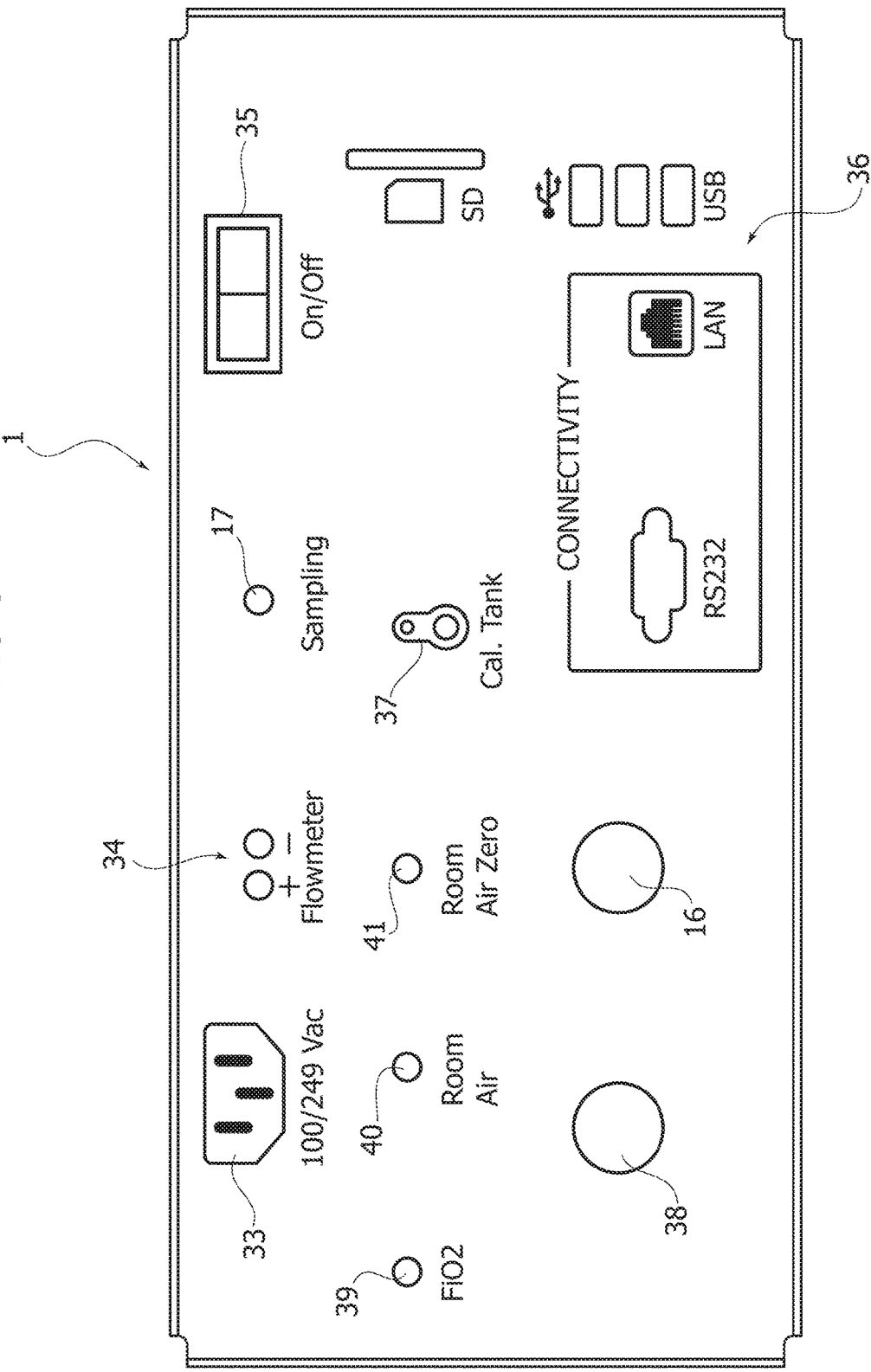

A preferred embodiment of the invention is shown in the annexed drawings in which:

FIG. 1 is a diagrammatic view which shows the device according to the invention connected to a subject able of breathing spontaneously and to a subject undergoing assisted pulmonary ventilation, FIG. 2 shows a block diagram of the device of FIG. 1, FIG. 3 shows a lateral face of an exemplary embodiment the device of the invention.

In FIG. 1 a device according to the invention is designated by reference numeral 1. The device 1 is connected to a patient able of breathing spontaneously and designated by reference S. Subject S breathes spontaneously inside a canopy into which ambient air is fed and diluted with the air exhaled by the subject S to be then fed through a corrugated tube 2 to a first inlet connector 16 (shown in FIGS. 2 and 3) of device 1.

As also shown in FIG. 1, the device 1 can be also connected to a patient T which is undergoing assisted pulmonary ventilation. Through the assisted pulmonary ventilation technique, subject T receives and transmits air through an endotracheal tube to which a bacterial filter 4 is associated. Air drawn from the patient T is "blown" into patient T by a ventilator device designated by reference numeral 6.

Naturally, FIG. 1 is a purely theoretical drawing and is intended to simply show the ability of the device according to the invention to operate each time on a S-type patient or a T-type patient.

The ventilator device 6 further includes two lines 61, 62 through which main portions of the air exhaled and inhaled by subject T respectively flow. A sampling portion of the air exhaled by subject T flows through a sampling line L1 which has one end connected to the bacterial filter 4 and the opposite end connected to a second inlet connector 17 (shown in FIGS. 2 and 3) of device 1.

To the device 1 there is associated a disposable flowmeter 5, which is interposed between the bacterial filter 4 and the ventilator device 6. As will be shown more in detail in the following with reference to FIG. 2, device 1 includes two pressure probes 51, 52 connected to the inlet and the outlet of flowmeter 5, respectively, through lines L8, L9. As will be also indicated in the following, the probes 51, 52 are associated to a differential pressure transducer 28.

As discussed in the foregoing, the device 1 can thus receive an air flow exhaled either by a subject S able of breathing spontaneously or by a subject T undergoing assisted pulmonary ventilation and therefore the device can selectively perform measurements of the metabolism on both types of patients.

As shown in the diagrammatic view of FIG. 1, device 1 has reduced dimensions and can rest on a structure 8 adapted to enable easy transportation. Naturally, all these details of construction may widely vary within the scope of the general principles forming the subject of the present invention. Furthermore, according to a preferred feature of the invention, the device 1 includes a display D on its front face for displaying all the information data provided by device 1.

FIG. 2 diagrammatically shows the essential components of device 1 and their connections, according to a preferred embodiment.

The device of the invention is able to perform all the functions for providing the required measurements and for calibrating the device 1, both in case of a connection to a subject S able of breathing spontaneously and in case of a connection to a subject T undergoing assisted pulmonary ventilation.

As shown in FIG. 2, the device 1 includes a main line L for passage of a sampling flow of the air exhaled by subject S or subject T.

In the main line L there is inserted a suction pump 9 providing a substantially constant flow rate. The suction pump 9 has the function of drawing an air flow into the main line L. In the main line L, upstream of the suction pump 9, there is provided a mixing mini-chamber 10. The mixing mini-chamber 10 serves for accumulating and mixing, within a number of a respiratory cycles, a plurality of sampling flows of the air exhaled by subject S or subject T, which come from tube 2 or line L1, respectively connected to the inlet connectors 16 and 17.

The device 1 is arranged so that the mixing mini-chamber 10 receives a sampling flow which constitutes only a portion of the flow exhaled by the subject. In this manner, a mixing chamber of reduced dimensions can be used, so that a functional device is obtained which is easy to be transported and used at the patient's site. In the present description, and in the following claims, the term "mixing mini-chamber" must be understood as indicating a mixing chamber having dimensions lower than those which would be required in the case said chamber should receive the entire air flow exhaled by the subject, at each respiratory cycle of the subject.

The device 1 further comprises a by-pass line LB arranged in parallel to the mixing mini-chamber 10, through which the air flow exhaled by subject S, T can flow without passing through the mixing mini-chamber 10. Also in the main line L, downstream of the mixing mini-chamber 10, there is arranged a by-pass valve 12 which can be selectively moved in two different positions. Through this selection, the airflow through the main line L can be caused to pass through the mixing mini-chamber 10 or through the by-pass line LB.

The device 1 further comprises, also along the main line L, sensor means 13 for sensing the oxygen concentration and sensor means 14 for sensing the carbon dioxide concentration, for respectively measuring the concentration of oxygen and carbon dioxide within the air flow through the main line L, downstream of the mixing mini-chamber 10. These sensor means can be constituted by sensor devices for sensing the oxygen concentration and the carbon dioxide concentration of any known type.

Downstream of sensor means 13, 14 there is interposed a switching valve 15 which switches the suction inlet of the suction pump 9 between a condition in which the suction pump 9 is connected to the sensor means 13, 14 and a condition in which this connection is interrupted.

The device 1 further comprises an electronic control unit E which receives and processes signals coming from sensor means 13, 14 in order to obtain a measurement of the oxygen consumption and the production of carbon dioxide by subject S or subject T during a number of respiratory cycles.

The electronic control unit E is configured also for controlling the switching valve 15 in a PWM (Pulse Width Modulation) mode, so as to determine a flow rate of the suction pump 9 which varies proportionally to the variation of the air flow during each respiratory cycle of subject T, whereas during the measurements on patient S, the switching valve 15 is controlled in order to determine a constant sampling flow rate. In this manner, the measurement carried out by device 1 is precise and reliable notwithstanding the sampling flow through the main line L constitutes only a portion of the total airflow exhaled by subject S or T. As indicated in the foregoing, it is thus possible, also for this reason, to provide a mixing chamber 10 with reduced dimensions which enables a device to be obtained which is a small and extremely functional in use, with no negative effects on the efficiency and precision of the measurement operation which must be carried out.

Again with reference to FIG. 2, the device 1 comprises a selection valve 18 which is interposed in the main line L upstream of the mixing mini-chamber 10. The selection valve 18 selectively connects the first connector 16 or the second connector 17 to the main line L, so that a measurement can be carried out selectively on a subject S or a subject T.

The selection valve 18 has an outlet 18a which is connected to the main line L, a first inlet 18b connected to the first connector 16 and therefore to subject S, and the second inlet 18c which can be connected by the sampling line L1 to the second connector 17 and therefore to the subject T.

Again with reference to FIG. 2, the device 1 comprises a calibration line L2. The sensor means 13, 14 require calibration operations and, for this purpose, line L2 receives a calibration flow. To this end, a switching valve 19 selectively connects the second inlet 18c of the selection valve 18 to the second connector 17 or to the calibration line L2. During normal operation of device 1, the selection valve 18 is switched to a position in which a sampling flow of the air exhaled by subject S or subject T, respectively coming from connector 16 or connector 17, reaches the main line L.

Also according to the normal operation of device 1, the by-pass valve 12 is in a position which causes the air flow to pass through the mixing mini-chamber 10, so that the electronic control unit E is able to process signals coming from the sensor means 13, 14 for obtaining measurements of the oxygen consumption and the production of carbon dioxide by subject S or subject T within a number of respiratory cycles.

As also discussed in the foregoing, one of the advantages of device 1 according to the present invention is that of being able to perform automatic calibration operations which avoid long warm-up waiting times prior to the normal operation and prior to performing measurement of the metabolism of subject S or T, which would be unacceptable for the operator. To this end, the electronic control unit E is programmed also for automatically starting, upon switching on the device 1, a self-calibration step in which the switching valve 19 communicates the second inlet 18c of the selection valve 18 to the calibration line L2. Moreover, the selection valve 18 communicates its second inlet 18c to the main line L. As a result, during the automatic calibration step, which is alternative to the normal operation of device 1, the main line L is in communication with the calibration line L2. During this self-calibration step, the by-pass valve 12 is in a position which causes the sampling flow of the air exhaled by subject S or T to pass through the by-pass line LB, without passing through the mixing mini-chamber 10. The self-calibration step can therefore be carried out immediately on the basis of the flow coming from the calibration line L2, since a filling of the mixing mini-chamber 10 is not required.

According to the preferred embodiment of the invention which is shown in FIG. 2, device 1 comprises a plurality of selector valves 21, 22, 23 which are distributed in series along said calibration line L2, for selectively connecting the calibration line L2 each time with only one among a plurality of auxiliary lines L3, L4, L5, L10 adapted to provide respective calibration data. The selector valves 21, 22, 23 are distributed in series along the calibration line L2 and each have a switching element movable between an active position, in which the selector valve communicates the respective auxiliary line to the calibration line L2 and an inactive position, in which the respective auxiliary line is isolated.

Each of these selector valves is shown only diagrammatically in the figure, while it must be understood that it can be made in the form of a solenoid valve of any known type adapted to this purpose, with a solenoid controlled by the electronic unit E.

A line FiO2, designated by reference L3, is provided for enabling the percentage of oxygen in the air supplied by the ventilator device 6 and drawn by subject T to be measured. Line L3 has a portion outside device 1 which is respectively connected at one end to the ventilator device 6 (as shown in FIG. 1) and at its opposite end to the inlet 39 which is provided, in the case of the example illustrated in FIGS. 1 and 3, on a lateral face of device 1. Line L3 of device 1 can be connected to the calibration line L2 through a first selector valve 21.

Again with reference to FIG. 2, also a first line L4 for taking ambient air is provided, in order to enable a detection of the composition of the ambient air. The ambient air flows into the device 1 and through line L4 through an inlet 40 provided on one side face of device 1, as shown in FIG. 3. Line L4 within device 1 can be connected to the calibration line L2 through a second selector valve 22. Also with reference to FIG. 2, a second line L5 for taking ambient air is provided, in which a means 20 for absorbing carbon dioxide is interposed. The carbon dioxide absorbing means 20 serves for totally removing the carbon dioxide content from the air flow which enters at a second ambient air inlet 41 (shown in FIG. 3) and comes to the second line L5 for taking ambient air, so as to enable a calibration of the zero level of the sensor means 14 for sensing the carbon dioxide concentration, which are arranged along the main line L. Line L5 can be connected to the calibration line L2 through a third selector valve 23.

Also with reference to the embodiment of FIG. 2, the first inlet 18b of the selection valve 18 is connected to the first inlet connector 16 through a second sampling line L6. The second sampling line L6 takes a portion of the flow exhaled by the subject S which breathes spontaneously and which is introduced into the first inlet connector 16 through the corrugated tube 2. On the sampling line L6 downstream of the first connector 16 there is provided a centrifugal pump 25 which takes the entire airflow which is introduced into the first inlet connector 16 at its inlet. In the preferred embodiment according to the invention, the pump 25 is a centrifugal pump, but it can be a pump of any other known type, which is able to perform its required function. The centrifugal pump 25 has an outlet which is connect both to the second sampling line L6 and to a discharge line L7 which discharges the most part of the airflow exhaled by subject S towards the outside.

Downstream of the centrifugal pump 25, with respect to the first connector 16, there is provided a turbine flowmeter 26 which measures the quantity of the airflow going out from the canopy (dilution flow). Also in this case, the flowmeter, in the preferred embodiment of the invention, is of the turbine type, although it can be of any known type.

To the device 1 there is further associated, as indicated in the foregoing, a disposable flowmeter or pneumotachograph 5 which is interposed between the bacterial filter 4 and the ventilator device 6. The device 1 includes two pressure probes 51, 52 (shown in FIG. 2) connected to the inlet and the outlet of the flowmeter 5, through two lines L8, L9, respectively. The two pressure probes 51, 52 communicate with a differential pressure transducer 28 arranged inside the device 1. Furthermore, again with reference to FIG. 2, along lines L8, L9, there are respectively interposed two valves 29, 30 for the automatic calibration of the disposable flowmeter 5. During the operation, the electronic unit E periodically causes a shifting of the valves 29, 30 to the positions in which they connect both probes 51, 52 with the atmosphere (thus connecting both of them to the same pressure) in order to enable a calibration of the zero of the differential pressure transducer 28 to be obtained.

A further feature of the device 1 according to the present invention lies in that the first inlet connector 16 of device 1 is also provided for being temporarily connected to the outlet of the disposable flowmeter 5 during a preliminary semi-automatic calibration of the disposable flowmeter 5. As a result, the electronic control unit E is also programmed for performing the preliminary semi-automatic calibration of the disposable flowmeter in which the centrifugal pump is activated for activating an air flow entering into the inlet connector 16 through the disposable flowmeter 5, and thus using the signal coming from the turbine flowmeter 26 in order to perform a set-up of the disposable flowmeter 5. Due to that the device 1 according to the present invention is able to perform this semi-automatic calibration step of the disposable flowmeter 5, the device 1 is thus able to avoid the use of a calibration syringe, differently from the known devices, with no prejudice for the hygiene required for clinical applications.

Finally, again with reference to FIG. 2, the device 1 comprises also sensor means 31 for sensing the humidity of the air flow which flows through the main line L and further humidity sensor means 32 which detect the humidity of the ambient air. The electronic control unit E is programmed also for comparing the humidity values measured by the sensor means 31, 32 and for activating an alarm signal visible on display D of device 1, when the difference between these values overcomes a predetermined threshold value.

FIG. 3 shows a lateral face of device 1 according to the present invention in which a plurality of connection inlets are provided which are necessary for the operation of device 1. Reference numeral 35 designates a switch on/off bottom for device 1. Reference 33 designates the inlet for a supply cable associated to device 1, which is not shown. Reference 36 designates a plurality of inlets for outer memory devices and web connections. Also with reference to FIG. 3, the second inlet 17 is visible which can be connected through the sampling line L1 to subject T. Also with reference to FIG. 3, the first inlet connector 16 is shown which can be connected to the subject S which breathes spontaneously.

Furthermore, reference numeral 34 designates the inlets of lines L8, L9 which can be connected to the disposable flowmeter 5 outside the device 1 and which are also connected to the differential pressure transducer 28 inside the device 1. Reference numeral 38 designates the outlet of line L7. Reference numeral 39 designates the inlet of line L3 which at its end opposite to device 1 is connected to the ventilator device 6 (as shown in FIG. 1).

Finally, also with reference to FIG. 3, numeral 33 designates an inlet communicating with a detection line L102 inside the device 1, which can be connected to a tank 42 (diagrammatically shown in FIG. 2) containing air having a known composition. This connection to the tank 42 is used for performing automatic calibrations of the sensor means for sensing the concentration of oxygen and carbon dioxide 13, 14.

Due to the above described features of the preferred embodiment of the invention, the device 1 is able of performing an average measurement of basal metabolism, both on subjects able of breathing spontaneously and on subjects who undergo assisted pulmonary ventilation, while avoiding long warm-up times through quick automatic calibration operations. Furthermore, also a semi-automatic calibration operation of the disposable flowmeter 5 can be performed rapidly, easily and precisely.

Naturally, while the principle of the invention remains the same, the details of construction and the embodiments may widely vary with respect to what has been described and illustrated purely by way of example, without departing from the scope of the present invention as defined in the following claims.

What is claimed is:

1. Device for the analysis of the air exhaled by a subject in order to measure basal metabolism of the subject, the device comprising:
    a main line, for passage of a sampling flow of the air exhaled by the subject,
    a suction pump having a substantially constant flow rate, said pump being arranged downstream of the main line, for drawing said sampling air flow into the main line,
    a mixing mini-chamber interposed in the main line upstream of the suction pump for accumulating or mixing with each other a plurality of air sampling flows exhaled by the subject within a number of respiratory cycles,
    a by-pass line arranged in parallel to the mixing mini-chamber through which the air flow can flow without passing through said mixing mini-chamber,
    a by-pass valve interposed in the main line downstream of the mixing mini-chamber and selectively displaceable in two different positions for causing the airflow through the main line to flow either through the mixing mini-chamber or through said by-pass line,
    first sensor means for sensing the oxygen concentration and second sensor means for sensing the carbon dioxide concentration, said first and second sensor means being arranged in the main line between said by-pass valve and the suction pump, for measuring the oxygen concentration and the carbon dioxide concentration within the air flow through the main line downstream of the mixing mini-chamber,
    a first switching valve for switching the suction inlet of the suction pump between a condition of connection to said first and second sensor means and a condition in which this connection is interrupted,
    flow measuring means for detecting the flow rate of the air inhaled or exhaled by the subject, and
    an electronic controller configured for:
    receiving and processing signals emitted by said first sensor means of the oxygen concentration, by said second sensor means of the carbon dioxide concentration and by said flow measuring means so as to obtain a measurement of oxygen consumption and carbon dioxide production by the subject within a number of respiratory cycles,
    wherein said device further comprises:
    a first inlet connector connected to a system for taking a flow of air exhaled by a subject who breathes spontaneously,
    a second inlet connector connected through a sampling line to a system for taking a flow of air exhaled by a subject undergoing assisted pulmonary ventilation,
    a selection valve interposed in the main line upstream of the mixing mini-chamber for selectively connecting said first connector or said second connector to said main line,
    said selection valve having an outlet connected to the main line, a first inlet connected to said first connector and the second inlet for connection to said second connector,
    a calibration line, which receives a calibration flow, to be used for calibrating said first and second sensor means for sensing the oxygen concentration and the carbon dioxide concentration,
    a second switching valve adapted to be switched between a sampling state and a calibration state, said switching valve being controlled by said electronic controller for selectively connecting said second inlet of said selection valve to said sampling line connected to said second connector or to said calibration line,
    a plurality of selector valves distributed in series along said calibration line for selectively connecting the calibration line each time to one only among a plurality of auxiliary lines adapted to provide respective calibration data,
    said electronic controller being configured so that, during normal operation of the device, the selection valve is switched for feeding to the main line either a sampling flow of the air exhaled by a subject who breathes spontaneously or by a subject which undergoes assisted pulmonary ventilation, said by-pass valve being in a position causing the airflow to pass through said mixing mini-chamber so that said electronic controller is able to perform said processing in order to obtain said measurement of the oxygen consumption and the carbon dioxide production by the subject within a number of respiratory cycles,
    said electronic controller being further programmed for automatically starting, upon switching on the device, a self-calibration stage of the device in which:
    the second switching valve communicates said second connector of said selection valve to said calibration line while the selection valve communicates its second inlet to said main line, so that the main line enters into communication with said calibration line,
    said electronic controller being configured so that in said self-calibration stage the by-pass valve is in a position which causes said sampling flow of the air exhaled by the subject to flow through said by-pass line, without passing through said mixing mini-chamber, whereby the self-calibration stage can be carried out immediately on the basis of the flow coming from said calibration line, without requiring a filling of said mixing mini-chamber.

2. Device according to claim 1, wherein said control unit is programmed so that:
    when the device operates with a subject undergoing assisted pulmonary ventilation, said electronic unit controls said first switching valve in a Pulse Width Modulation (PWM) mode, in order to determine a flow rate of the suction pump which varies in proportion to the variation of the flow during the respiratory cycle of the subject,
    whereas when the device operates with a subject who breathes spontaneously, said electronic unit controls the first switching valve in order to determine a constant sampling flow rate, so as to ensure in any case a substantial precision of said measurement, notwithstanding said sampling flow constitutes only a fraction of the total flow of the air exhaled by the subject.

3. Device according to claim 1, wherein said auxiliary lines comprise:
- a Fraction of inspired oxygen (FiO2) line connected to a line which feeds air to a subject undergoing assisted pulmonary ventilation, to enable a detection of the percentage of oxygen present in the air inhaled by the subject undergoing assisted pulmonary ventilation,
- a first line for taking ambient air to enable a detection of the composition of the ambient air, said first line for taking the air being used in the case of measurement of basal metabolism on a subject who breathes spontaneously,
- a second line for taking ambient air, in which a means is interposed for absorbing carbon dioxide, adapted to remove completely the carbon dioxide content from the air flow which flows through said second line for taking ambient air, in order to enable a zero-calibration for said second sensor means for sensing the carbon dioxide concentration,
- a line which can be connected to a tank containing air of known composition, to enable automatic calibrations of the first and second sensor means for sensing the oxygen concentration and the carbon dioxide concentration.

4. Device according to claim 3, wherein each of said selector valves distributed in series along the calibration line has a switching element which can be moved between an active position, in which the selector valve communicates a respective auxiliary line to the calibration line and an inactive position in which the respective auxiliary line is isolated.

5. Device according to claim 1, wherein said first inlet of the selection valve is connected to said first inlet connector by a second sampling line through which a sampling portion is taken of the air flow exhaled by the subject who breathes spontaneously, said flow portion being introduced into said first inlet connector.

6. Device according to claim 5, wherein said second sampling line is connected to said first connector through:
- a centrifugal pump which at its inlet takes the entire air flow which is introduced into the first inlet connector said centrifugal pump further including an outlet which is connected both to said second sampling line and to a discharged line adapted to discharge most part of the airflow which is exhaled by the subject which breathes spontaneously towards the outside,
- a first turbine flowmeter for measuring the entire flow rate of the air exhaled by the subject who breathes spontaneously, a part of which reaches said first inlet of the selection valve.

7. Device according to claim 1, wherein said flow measuring means comprise:
- a second disposable flowmeter or pneumotachograph which is to be interposed in a line which feeds air to a subject undergoing assisted pulmonary ventilation, said second flowmeter comprising two pressure probes at an inlet and an outlet of the second flowmeter, which are respectively connected to two inlets of a differential pressure transducer, for detecting the flow rate of the air flow through said second flowmeter.

8. Device according to claim 7, wherein said device includes two valves for automatic calibration of said second disposable flowmeter which are adapted to periodically communicate the two inlets of said differential pressure transducer to the atmosphere, so as to enable a zero-calibration of said transducer.

9. Device according to claim 6, wherein:
- said first inlet connector of the device is adapted to be temporarily connected to the outlet of said second disposable flowmeter in a preliminary semi-automatic calibration stage of the second disposable flowmeter, and in that
- said electronic controller is further programmed for performing said preliminary calibration of the second disposable flowmeter by activating said centrifugal pump for causing an air flow to be fed to said inlet connector through said second disposable flowmeter and by using a signal from said first turbine flowmeter for performing a set-up of the second disposable flowmeter.

10. Device according to claim 1, wherein said electronic controller is further programmed for receiving and processing signals coming from said first sensor means for sensing the oxygen concentration and from said second sensor means for sensing the carbon dioxide concentration during an operative stage with static flow, in which said switching valve is in a condition in which the connection of said suction pump to said first and second sensor means is interrupted, so that no dynamic flow occurs through the sensor means.

11. Device according to claim 1, wherein the device further comprises:
- first humidity sensor means for sensing humidity of the air flow through the main line and
- second humidity sensor means adapted to detect humidity of the ambient air,
- said electronic controller being further programmed for comparing the humidity values measured by said first and second humidity sensor means and for activating an alarm signal when the difference between these values overcomes a predetermined threshold.

12. Method for the analysis of the air exhaled by a subject in order to measure basal metabolism of the subject with the use of the device according to claim 1, in which during the normal operation of the device said selection valve is switched so as to feed into the main line a sampling flow of the air exhaled by the subject who breathes spontaneously or by a subject which undergoes assisted pulmonary ventilation, said by-pass valve being in its position causing the air flow to pass through said mixing mini-chamber so that said electronic control unit is able to perform said processing in order to obtain said measurement of the oxygen consumption and the carbon dioxide production by the subject within a number of respiratory cycles,
- wherein said method further comprises the step of starting automatically, upon switching on the device, a self-calibration stage of the device in which:
  - the second switching valve communicates said second inlet of said selection valve to said calibration line and the selection valve communicates its second inlet to said main line, so that the main line enters into communication with said calibration line,
  - in said self-calibration stage, the by-pass valve is in the position which causes said sampling flow of the air exhaled by the subject to flow through said by-pass line without passing through said mixing mini-chamber, so that the self-calibration stage can be performed immediately on the basis of the flow coming from said calibration line, without requiring a filling of said mixing mini-chamber.

13. Method for the analysis of the air exhaled by a subject in order to measure basal metabolism of the subject with the use of the device according to claim 6, wherein two valves are provided for automatic calibration of said second disposable flowmeter, which valves periodically communicate two inlets of said differential pressure transducer to the atmosphere, so as to enable a zero-calibration of said transducer.

14. Method for the analysis of the air exhaled by a subject in order to measure basal metabolism of the subject with the use of the device according to claim 6, wherein said second disposable flowmeter is temporarily connected with its outlet to said first inlet connector of the device in a preliminary semi-automatic calibration stage of the second disposable flowmeter, and in that said preliminary calibration of the second disposable flowmeter is performed by actuating said centrifugal pump in order to activate an air flow towards said inlet connector through said second disposable flowmeter and by using a signal coming from said first turbine flowmeter for performing a set-up of the second disposable flowmeter.

* * * * *